United States Patent [19]
Masuda et al.

[11] Patent Number: 5,578,845
[45] Date of Patent: Nov. 26, 1996

[54] DIELECTRIC THIN FILM DEVICE WITH LEAD ERBIUM ZIRCONATE TITANATE

[75] Inventors: Yoshiyuki Masuda, Noda; Yasushi Ogimoto, Nagareyama; Noboru Ootani, Tokyo, all of Japan

[73] Assignee: Sharp Kabushiki Kaisha, Osaka, Japan

[21] Appl. No.: 264,060

[22] Filed: Jun. 22, 1994

[30] Foreign Application Priority Data

Jun. 23, 1993 [JP] Japan .................................. 5-152206
Jun. 15, 1994 [JP] Japan .................................. 6-133156

[51] Int. Cl.$^6$ .................. H01L 27/108; H01L 29/76; H01L 29/94; H01L 31/119
[52] U.S. Cl. .................. 257/295; 257/296; 257/301; 257/310; 257/417; 257/418; 257/443; 423/593; 365/65; 365/117; 365/145; 359/248; 73/514.16; 73/514.21; 73/514.34; 73/514.36
[58] Field of Search .................. 257/295, 310, 257/296, 301, 306, 417, 418; 365/145, 117, 65; 423/593; 359/248; 73/514.16, 514.21, 514.34, 514.36

[56] References Cited

U.S. PATENT DOCUMENTS 5,112,433  5/1992  Dawson et al. .................. 423/593

FOREIGN PATENT DOCUMENTS

| | | |
|---|---|---|
| 0375594 | 6/1990 | European Pat. Off. . |
| 0485907 | 5/1992 | European Pat. Off. . |
| 0516031 | 12/1992 | European Pat. Off. . |
| 48-76098 | 10/1973 | Japan . |
| 63-151672 | 6/1988 | Japan . |

OTHER PUBLICATIONS

Hirano et al., *Third Euro-Ceramics*, "Processing of Better . . . ," vol. 2, pp. 685–698, Sep. 12, 1993, Faenza Editrice Iberica, Spain.

M. N. Kamalasanan et al., "Dielectric and ferroelectric properties . . . ," *J. Appl. Phys.* 74(9), Nov. 1, 1993, pp. 5679–5686.

Reza Moazzami et al., IEEE Transactions on Electron Devices, vol. 39, No. 9, pp. 2044–2049 (Sep., 1992).

R. E. Jones et al., Appl. Phys. Lett. 60(8), pp. 1022–1024 (Feb. 24, 1992).

*Primary Examiner*—William Mintel

[57] ABSTRACT

A dielectric thin film device is constructed by a dielectric thin film using lead erbium zirconate titanate represented by $(Pb_{1-y}Er_y)(Zr_xTi_{1-x})O_3$ with $0<x<1$ and $0<y<1$. This dielectric thin film element has excellent electric characteristics of a leak electric current and fatigue characteristics, etc. The dielectric thin film element may have a thermally grown silicon dioxide film, a titanium film, a platinum lower electrode, a film of lead erbium zirconate titanate represented by $(Pb_{1-y}Er_y)(Zr_xTi_{1-x})O_3$ and a platinum upper electrode. These films and electrodes are sequentially formed on an n-type silicon substrate. In this case, $0.45 \leq x \leq 0.75$ and $0.05 \leq y \leq 0.1$ are set. A method for manufacturing a dielectric thin film has the steps of coating a substrate with a precursor solution of erbium lead zirconate titanate represented by $(Pb_{1-y}Er_y)(Zr_xTi_{1-x})O_3$ drying the coated solution at a high temperature to obtain a dry gel; and thermally treating the dry gel at a higher temperature to produce the dielectric thin film is constructed of the lead erbium zirconate titanate represented by $(Pb_{1-y}Er_y)(Zr_xTi_{1-x})O_3$ with $0.45 \leq x \leq 0.8$ and $0.005 \leq y \leq 0.1$.

10 Claims, 13 Drawing Sheets

DIELECTRIC THIN FILM DEVICE WITH LEAD ERBIUM ZIRCONATE TITANATE

BACKGROUND OF THE INVENTION

1. Field of the Invention

The present invention relates to a dielectric thin film element used in a memory device, a pyroelectric device, a piezoelectric device, an electrooptic device, etc. Further, the present invention relates to a method for manufacturing the dielectric thin film used in such a dielectric thin film element.

2. Description of the Related Art

Recently, non-volatile semiconductor memory elements are attracting much public attention. These non-volatile semiconductor memory elements are represented by a read only memory (ROM), a programmable ROM (PROM), an erasable PROM (EPROM), an electrically erasable PROM (EEPROM), etc. In particular, the EEPROM is promising since stored contents of the EEPROM can be electrically rewritten. In the EEPROM, a trap region or a floating gate within a gate insulating film of a metal insulator semiconductor field effect transistor (MIS-FET) is charged by charge injection from a silicon substrate. The surface conductivity of the substrate is modulated by electrostatic induction of injected charges.

A ferroelectric non-volatile memory utilizing spontaneous polarization of a ferroelectric substance can be used as a non-volatile memory using a method completely different from the above known modulating method of the EEPROM. This ferroelectric non-volatile memory can have one of two structures, either a structure composed of an MFS (metal ferroelectric semiconductor)-FET (field effect transistor) structure or a capacitor structure.

In the MFS-FET structure, a gate insulating film of the MIS-FET is formed as a ferroelectric thin film. The conductivity of a semiconductor surface is modulated by charges induced on the semiconductor surface such that spontaneous polarization of a ferroelectric material is compensated in accordance with the direction and the magnitude of the spontaneous polarization. Memory contents are read by utilizing this modulation.

In the capacitor structure, a ferroelectric thin film is supported between two electrodes. Memory contents are read by detecting the existence or nonexistence of an inverted electric current caused by inverting the spontaneous polarization of the ferroelectric material.

For example, the ferroelectric material used for such a ferroelectric non-volatile memory can be lead zirconate titanate (which is called PZT in the following description), lead titanate ($PbTiO_3$), or barium titanate ($BaTiO_3$), etc. At present, the PZT material is being vigorously researched as a material for a most promising non-volatile memory.

A dynamic random access memory (DRA) appeared in 1970 as a charge storing solid state memory having a simple structure and manufactured by a simple manufacturing method. This DRAM is widely used while the degree of integration of the DRAM is increasing. In particular, a so-called 1Tr-1C DRAM is formed by constructing one capacitor and one transistor in one memory cell. After 1972, this 1Tr-1C DRAM has been most widely used since this DRAM has a simple shape and a small size. In this DRAM, a dielectric thin film capacitor stores charges and a transistor composed of a semiconductor is used as a switch for separating capacitors from each other.

The chip area is gradually increased as the DRAM is integrated. However, the cell area is further reduced in comparison with the increase in chip area. It is necessary to set a cell capacity (as an electrostatic capacity of the capacitor) required for the DRAM to about 30 fF ($3\times10^{-14}$ F) in consideration of sensitivity of a sense amplifier, a bit line capacitance, etc. even when the DRAM is integrated. An effective area S for the capacitor must be increased, or the thickness d of a capacitor thin film must be reduced to maintain an electrostatic capacity C of the capacitor at a certain value. Otherwise, a dielectric constant $\epsilon$ of a capacitor material must be increased to maintain the electrostatic capacity C of the capacitor at a certain value. Therefore, the effective area S for the capacitor is increased and the thickness d of the capacitor thin film is reduced with respect to a stacked type capacitor cell, a trenched type capacitor cell, etc. as a method for increasing the integration degree of the DRAM until the present time. However, in such a stereoscopic structure, the number of manufacturing processes increases and the yield is reduced by an increase in step height. Further, techniques for forming a thin film have already reached a limit. Accordingly, it is necessary to deposit a thin film of a dielectric substance having characteristics of a high dielectric constant $\epsilon$ on silicon (Si).

Changes in residual polarization and dielectric constant with respect to a Zr/Ti ratio in PZT are described in "Properties of D.C. magnetron-sputtered lead zirconate titanate thin films" Thin Solid Films, 172 (1989), pp. 251–267. In this case, the Zr/Ti ratio ranges from 50/50 to 70/30 and the residual polarization is set to $Pr \geq 10$ $\mu C/cm^2$.

However, dielectric characteristics of a dielectric thin film constituting the above general dielectric thin film element are not necessarily sufficient to obtain a practical dielectric thin film. In particular, it is necessary to reduce the leakage current generated between both electrodes supporting the dielectric thin film. Further, it is necessary to improve the electrical fatigue characteristics of the dielectric thin film. For example, a fourth element is added as a trial to a PZT material as a dielectric thin film material so as to improve the above electrical characteristics of the dielectric thin film. However, no dielectric thin film having high performance has been realized so far.

SUMMARY OF THE INVENTION

It is therefore an object of the present invention to provide a dielectric thin film element having excellent electric characteristics with low leakage current and good fatigue characteristics, and provide a method for manufacturing this dielectric thin film element.

The above object of the present invention can be achieved using a dielectric thin film element constructed by a dielectric thin film using lead erbium zirconate titanate represented by $(Pb_{1-y}Er_y)(Zr_xTi_{1-x})O_3$ where $0<x<1$ and $0<y<1$ are set.

In the present invention, the dielectric thin film of the dielectric thin film element preferably shows ferroelectricity, or has high dielectric constant characteristics.

The dielectric thin film element comprises a thermally grown silicon dioxide film, a titanium film, a platinum lower electrode, a film of lead erbium zirconate titanate represented by $(Pb_{1-y}Er_y)(Zr_xTi_{1-x})O_3$ and a platinum upper electrode. These films and electrodes are sequentially formed on an n-type silicon substrate. In this case, $0.45 \leq x \leq 0.75$ and $0.05 \leq y \leq 0.1$ are set.

A method for manufacturing the dielectric thin film comprises the steps of coating a substrate with a precursor solution of lead erbium zirconate titanate represented by $(Pb_{1-y}Er_y)(Zr_xTi_{1-x})O_3$; drying the coated solution at a high temperature to obtain a dry gel; and thermally treating the dry gel at a higher temperature. The dielectric thin film of lead erbium zirconate titanate represented by $(Pb_{1-y}Er_y)(Zr_xTi_{1-x})O_3$ and $0.45 \leq x \leq 0.8$ and $0.005 \leq y \leq 0.1$ are set.

In the dielectric thin film element of the present invention, a novel material of lead erbium zirconate titanate represented by $(Pb_{1-y}Er_y)(Zr_xTi_{1-x})O_3$ is used as the dielectric thin film for the first time. Accordingly, the dielectric thin film has excellent electric characteristics in which the leakage current generated between both electrodes supporting the dielectric thin film is small and fatigue caused by repeatedly using the dielectric thin film is reduced.

Further objects and advantages of the present invention will be apparent from the following description of the preferred embodiments of the present invention as illustrated in the accompanying drawings.

DESCRIPTION OF THE PREFERRED EMBODIMENTS

The preferred embodiments of a dielectric thin film element and the manufacturing method thereof in the present invention will next be described in detail with reference to the accompanying drawings.

Figure 1:
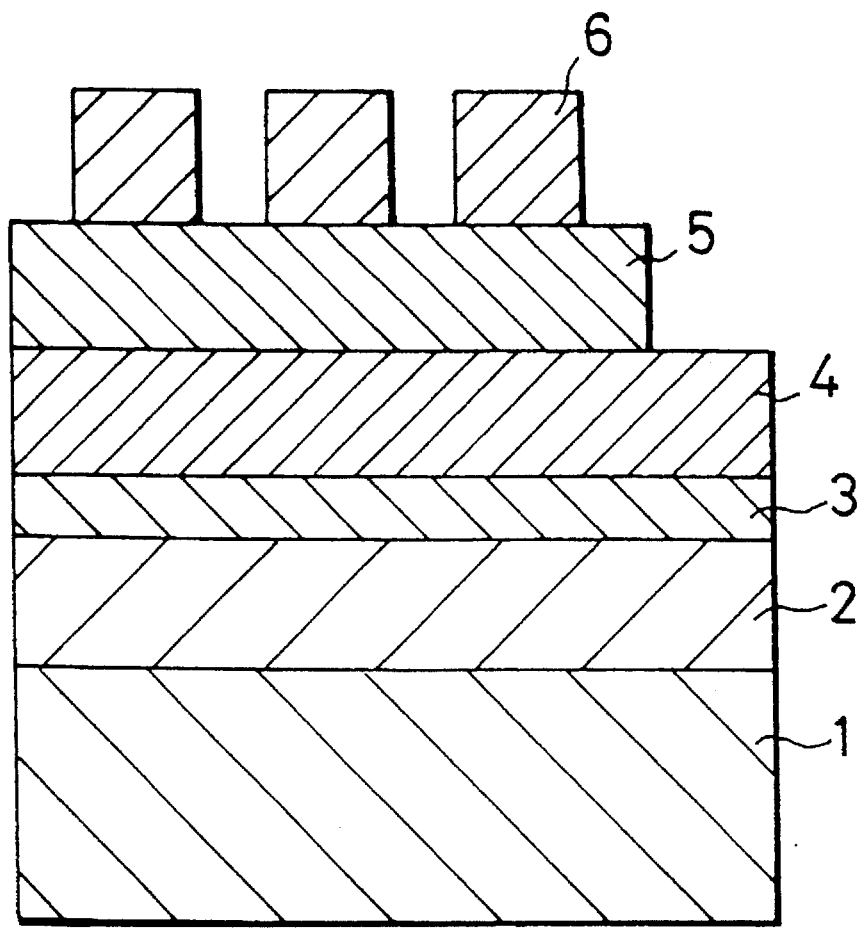
FIG. 1 is a main cross-sectional view showing the construction of the dielectric thin film element fabricated to evaluate the electrical characteristics of the dielectric thin film in accordance with one embodiment of the present invention.

FIG. 1 is a main cross-sectional view showing the structure of a dielectric thin film element constructed by a dielectric thin film in accordance with the first embodiment of the present invention. FIG. 1 shows a structure of the dielectric thin film element fabricated to evaluate the electrical characteristics described later. As shown in FIG. 1, a thermal silicon dioxide film 2, a titanium (Ti) film 3, a platinum (Pt) lower electrode 4, a dielectric thin film 5 of lead erbium zirconate titanate (called PEZT in the following description), and a platinum (Pt) upper electrode 6 are sequentially formed on an n-type silicon substrate 1.

A method for fabricating the dielectric thin film element shown in FIG. 1 will first be explained. The surface of an n-type silicon substrate 1 is thermally oxidized by a thermal oxidizing method so that a thermal silicon dioxide film 2 having 2000 Å in thickness is formed. A titanium (Ti) film 3 having 300 Å in thickness and a platinum (Pt) lower electrode 4 having 2000 Å in thickness are sequentially formed on this silicon dioxide film 2 by using a sputtering method. Thereafter, a PEZT dielectric thin film 5 is formed as described later. Then, platinum (Pt) upper electrodes 6 having 2000 Å in thickness are formed by a vacuum evaporation method or lift-off such that these platinum upper electrodes 6 are separated from each other and have an electrode size of 60 μm×60 μm. In the vacuum evaporation method, the platinum (Pt) upper electrodes 6 are formed through a mask.

The PEZT crystal structure is a perovskite structure and the PEZT is almost transparent with a yellow tinge.

A method for forming the PEZT dielectric thin film 5 will be subsequently explained. As mentioned above, the thermal silicon dioxide film 2, the titanium (Ti) film 3 and the platinum (Pt) lower electrode 4 are sequentially formed on the n-type silicon substrate 1. Thereafter, the PEZT dielectric thin film 5 having 2000 Å in thickness is formed by using a sol-gel method in which reproducibility of composition control is good even in a multiple component system.

In the sol-gel method, a solution of metal alkoxide is heated so that a composite alkoxide solution is formed. Further, water is added to this composite alkoxide solution to cause hydrolysis and condensation polymerization so that a precursor solution is made. This precursor solution is coated and formed on a substrate so that a polymer gel film is formed. This polymer gel film is dried and heated so that a thin film is formed.

Figure 2:
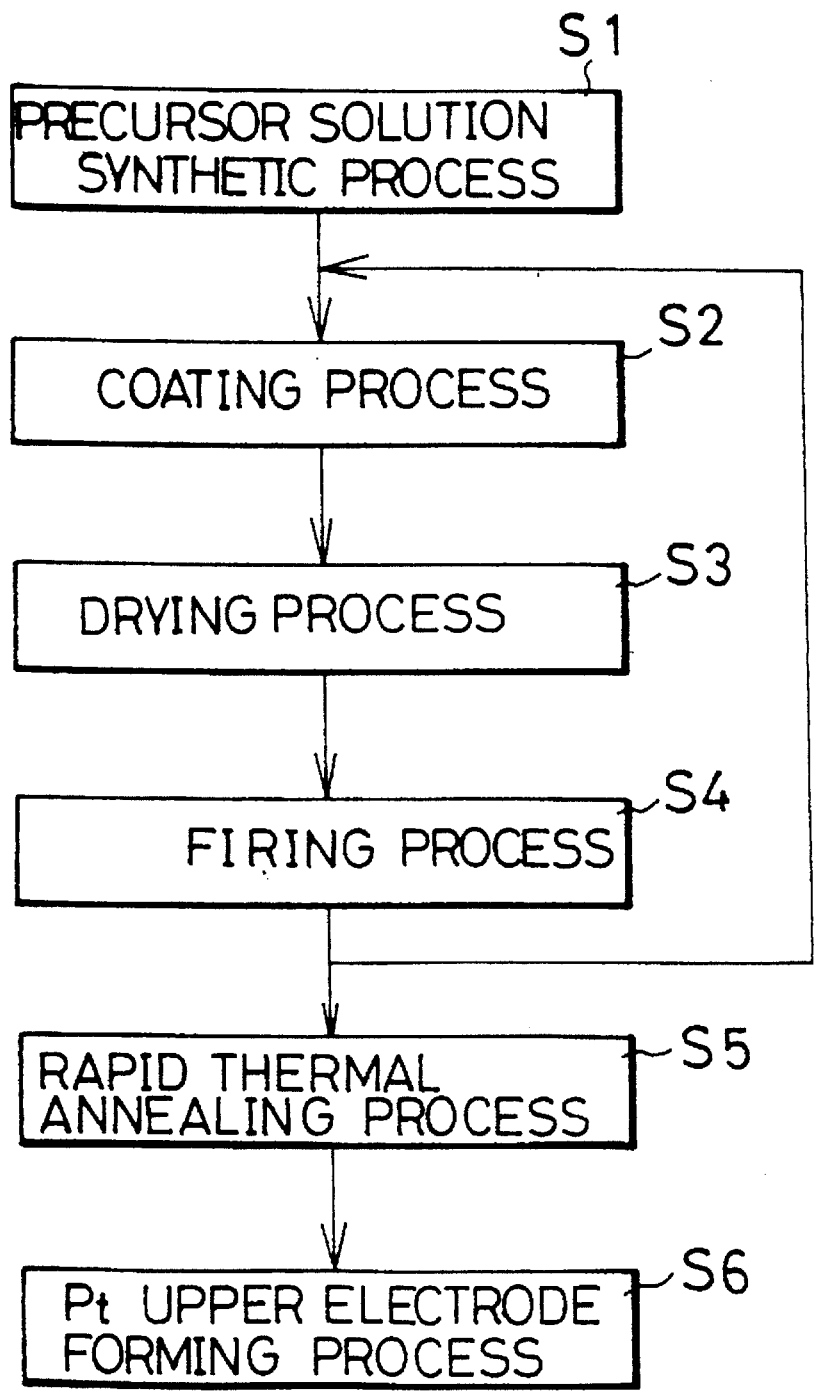
FIG. 2 is a flow chart showing processes for forming a PEZT dielectric thin film in this embodiment.

Processes for forming this PEZT dielectric thin film 5 will be explained next with reference to a flow chart shown in FIG. 2. Six kinds of PEZT precursor solutions having the following composition ratios are first synthesized. These precursors are used in the synthetic process S1 to manufacture six kinds of dielectric thin film elements having different composition ratios.

(1) Pb:Er=99.5:0.5, Zr:Ti=64:36

(2) Pb:Er=99:1, Zr:Ti=64:36

(3) Pb:Er=98:2, Zr:Ti=64:36

(4) Pb:Er=95:5, Zr:Ti=64:36

(5) Pb:Er=93:7, Zr:Ti=64:36

(6) Pb:Er=90:10, Zr:Ti=64:36

Accordingly, in a chemical formula $(Pb_{1-y}Er_y)(Zr_xTi_{1-x})O_3$, the PEZT precursor solutions having six kinds of composition ratios are made by setting x to 0.64 and setting y to 0.005, 0.01, 0.02, 0.05, 0.07 and 0.1.

Thus, the thermally grown silicon dioxide film 2, the titanium (Ti) film 3 and the platinum (Pt) lower electrode 4 are sequentially formed on the n-type silicon substrate 1. In a coating process S2, each of the above PEZT precursor solutions drops on the platinum (Pt) lower electrode 4. Further, each of the PEZT precursor solutions is deposited using a spin coating method. Initially, the substrate is rotated for 3 seconds at 350 rpm. Then, the substrate is rotated for 20 seconds at 5000 rpm. Thus, the platinum (Pt) lower electrode 4 is coated With the PEZT precursor solution. A dry gel thin film is obtained in a drying process S3 when each of the PEZT precursor solutions is dried by holding each of the examples coated with precursor for 15 minutes at a temperature of 100° C. In a heat treating process S4, each of the PEZT dry gel films is thermally treated by holding each of the PEZT dry gel films for 60 minutes at a temperature of 400° C. so that organic substances are thermally decomposed. The above processes S2 to S4 are repeated three times so that a PEZT dielectric thin film having about 2000 Å in thickness is obtained.

In a rapid thermal annealing process S5, the above PEZT dielectric thin film is annealed by using an infrared rapid thermal annealing system so that PEZT is crystallized.

The infrared rapid thermal annealing system is designed such that a furnace is formed in a horizontal pipe and an infrared ray is converged to a central portion of this pipe.

In this rapid thermal annealing process, the PEZT dielectric thin film is annealed for seconds at an annealing temperature of 650° C. and at atmospheric pressure in a 100% oxygen atmosphere. Thereafter, as mentioned above, a platinum (Pt) upper electrode 6 is formed so that a dielectric thin film element having the structure shown in FIG. 1 is fabricated. Thus, six kinds of dielectric thin film elements having different composition ratios of the PEZT as the dielectric thin film have been fabricated.

Figure 3:
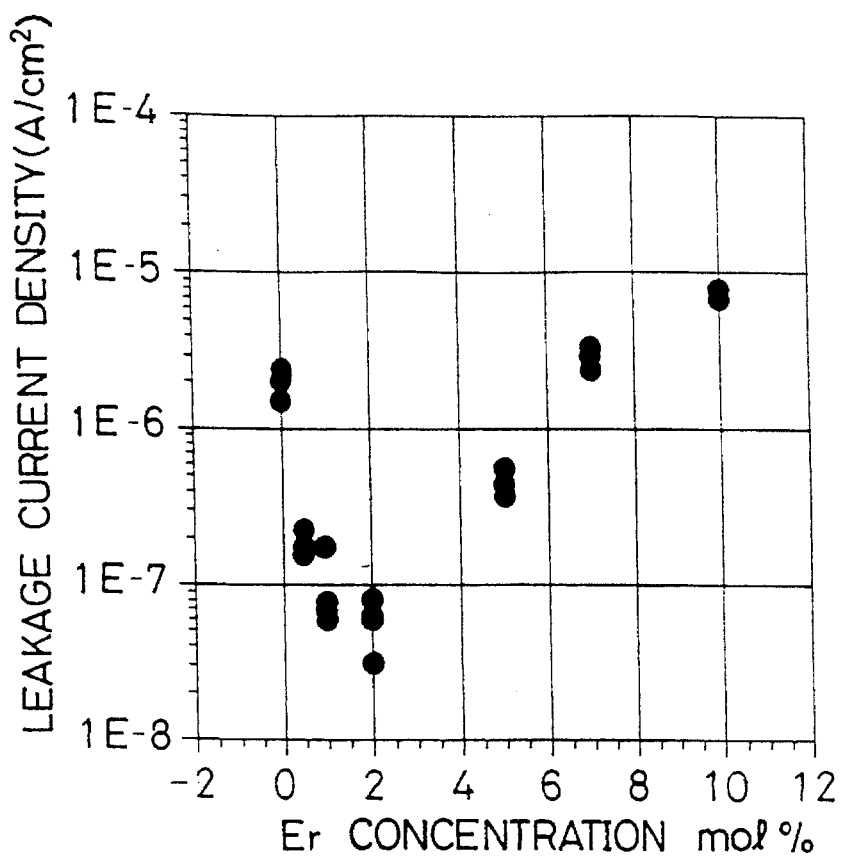
FIG. 3 is a graph showing measured results of the leakage current density of the dielectric thin film element in this embodiment.

Subsequently, evaluation of the electrical characteristics of each of the dielectric thin film elements fabricated above will be explained. FIG. 3 shows measured results of the leakage current of each of the dielectric thin film elements fabricated above. In FIG. 3, the abscissa shows the composition ratio of erbium (Er) of a PEZT dielectric thin film constituting each of the dielectric thin film elements. In FIG. 3, the ordinate shows a logarithmic value of the leakage current when a DC bias voltage of 3 V is applied between the platinum (Pt) lower electrode 4 and the platinum (Pt) upper electrode 6. In FIG. 3 several points are plotted which correspond to measurement from different upper electrodes 6.

In FIG. 3, the leakage current is ranged from $1.5 \times 10^{-7}$ to $2.5 \times 10^{-7}$ (A/cm$^2$) when the erbium (Er) composition ratio is equal to 0.5 (y=0.005). The leakage current ranged from $6 \times 10^{-8}$ to $7 \times 10^{-8}$ (A/cm$^2$) when the erbium composition ratio is equal to 1 (y=0.01). The leakage current ranged from $3 \times 10^{-8}$ to $8 \times 10^{-8}$ (A/cm$^2$) when the erbium composition ratio is equal to 2 (y=0.02). The leakage current ranged from $4 \times 10^{-7}$ to $6 \times 10^{-8}$ (A/cm$^2$) when the erbium composition ratio is equal to 5 (y=0.05). It should be understood that the leakage current is greatly reduced, by an order of magnitude or more in comparison with the leakage current value for comparison from $1 \times 10^{-6}$ to $3 \times 10^{-6}$ (A/cm$^2$) obtained from PZT when the erbium composition ratio is equal to 0 (y=0).

For example, PLZT for comparison is reported in "Electrical properties of PLZT thin films by a sol-gel method" on pp. 204–206 of "Extended Abstracts of the 1991 International Conference on Solid State Devices and Materials" in Yokohama, Japan. In these cases, the leakage current ranged from $8 \times 10^{-7}$ to $9 \times 10^{-7}$ (A/cm$^2$) when the molar fraction of lanthanum (La) is equal to 5 mol %, the film thickness 200 nm, and the applied voltage is equal to 1.65 V. It should be understood that for a film thickness of 200 nm the leakage current in the case of the PEZT is greatly reduced in comparison with the PLZT.

Figure 4:
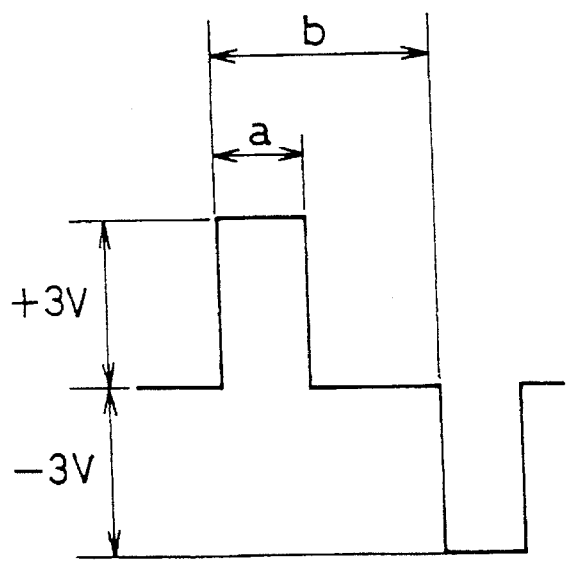
FIG. 4 is a view showing a waveform of a pulse applied to the dielectric thin film element when fatigue characteristics of the dielectric thin film element in this embodiment were measured.
Figure 5:
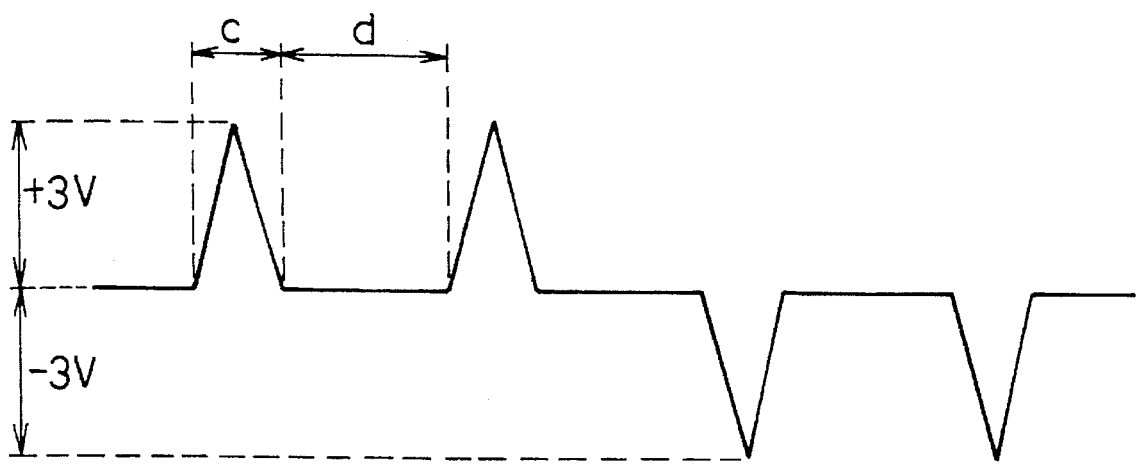
FIG. 5 is a view showing a waveform of a pulse applied to the dielectric thin film element when the hysteresis of the dielectric thin film element in this embodiment were measured.
Figure 6A:
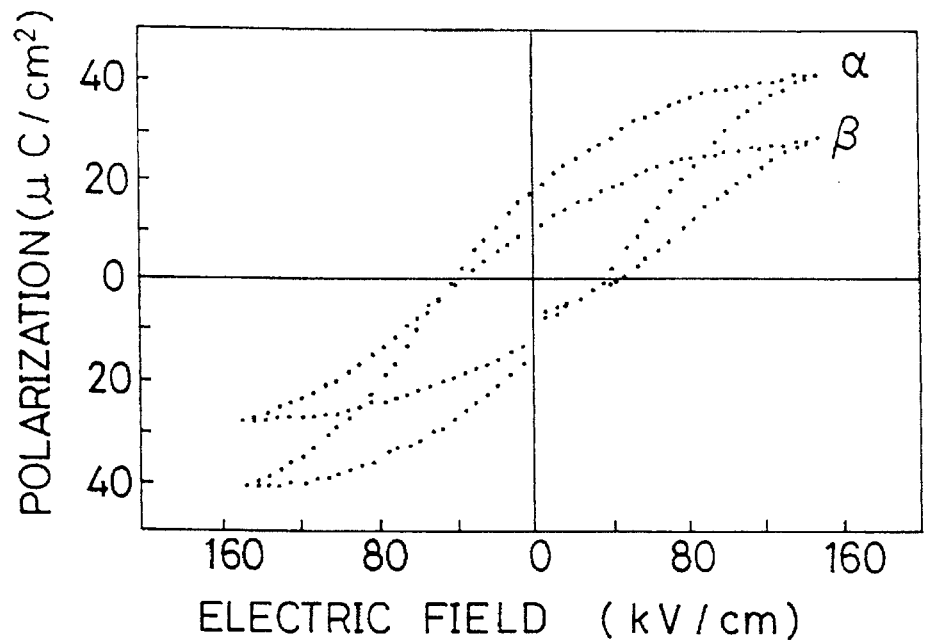
FIGS. 6a, 6c and 6d are a graphs showing the measured results of fatigue characteristics by hysteresis measurement for the PEZT dielectric thin film element in this embodiment.

Measurement of the fatigue characteristics of the PEZT films in the erbium composition ratio with y=0.01 will next be explained with respect to the dielectric thin film element fabricated above. Pulses having pulse widths of a=8.6 μsec and b=28.3 μsec are applied to this dielectric thin film element at voltages of ±3 V as shown in FIG. 4 between the platinum (Pt) lower electrode 4 and the platinum (Pt) upper electrode 6 in FIG. 1 so that polarization of the dielectric thin film element is inverted one hundred million times (10$^8$ times). Thereafter, a series of four pulses having pulse widths of c=2 msec and d=1 sec is applied to the dielectric thin film element at voltages of ±3 V as shown in FIG. 5. FIG. 6a shows the measured results of fatigue characteristics obtained by observing hysteresis loops before and after this polarization inversion.

In FIGS. 6a to 6d, the abscissa shows an electric field and the ordinate shows polarization. As can be seen from FIG. 6a, the dielectric thin film element (y=0.01) in this embodiment shows ferroelectricity drawing a hysteresis loop α in which remanent polarization is initially 15.78 (μC/cm$^2$) and a coercive field is 37.58 (kV/cm). After the polarization of the dielectric thin film element is inverted 10$^8$ times as mentioned above, the dielectric thin film element provides a hysteresis loop β in which the remanent polarization is 10.88 (μC/cm$^2$). Accordingly, a reduction in remanent polarization is small, about 4.5 (μC/cm$^2$) in the observed fatigue characteristics.

Figure 6B:
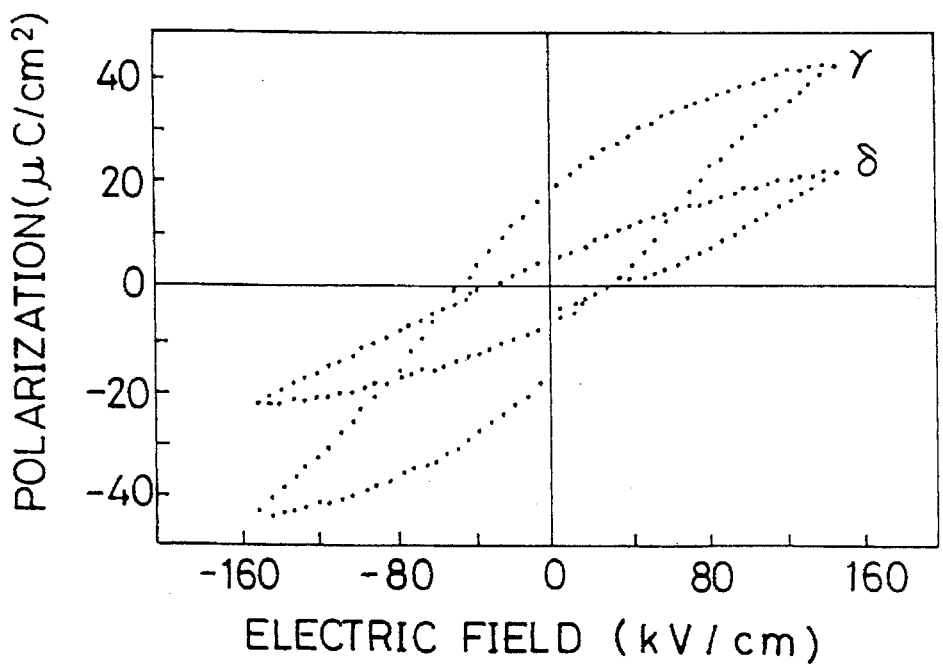
FIG. 6b is a graph showing measured results of fatigue characteristics by hysteresis measurement for a PZT dielectric thin film element.
Figure 6C:
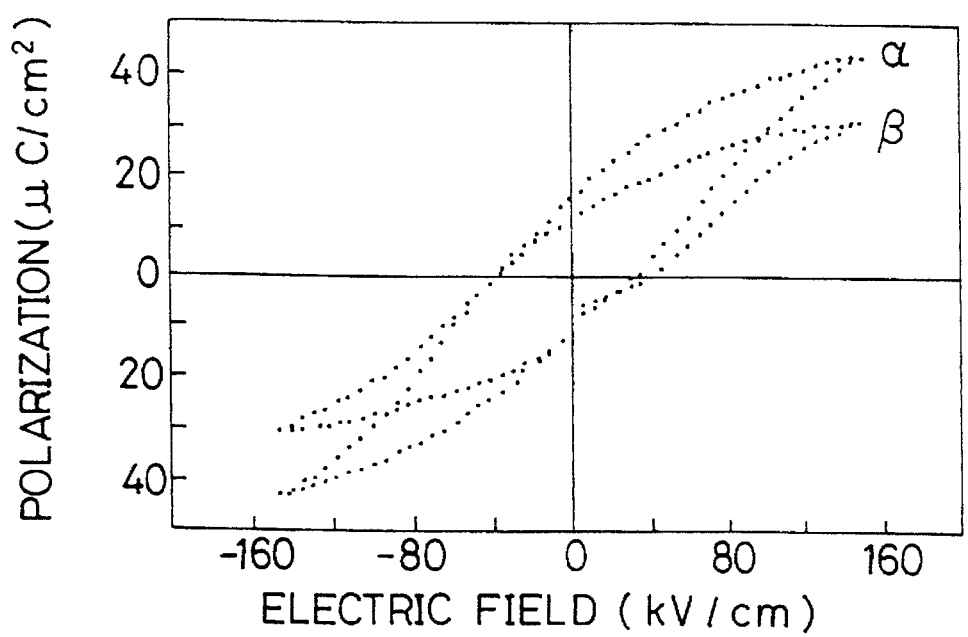
Figure 6D:
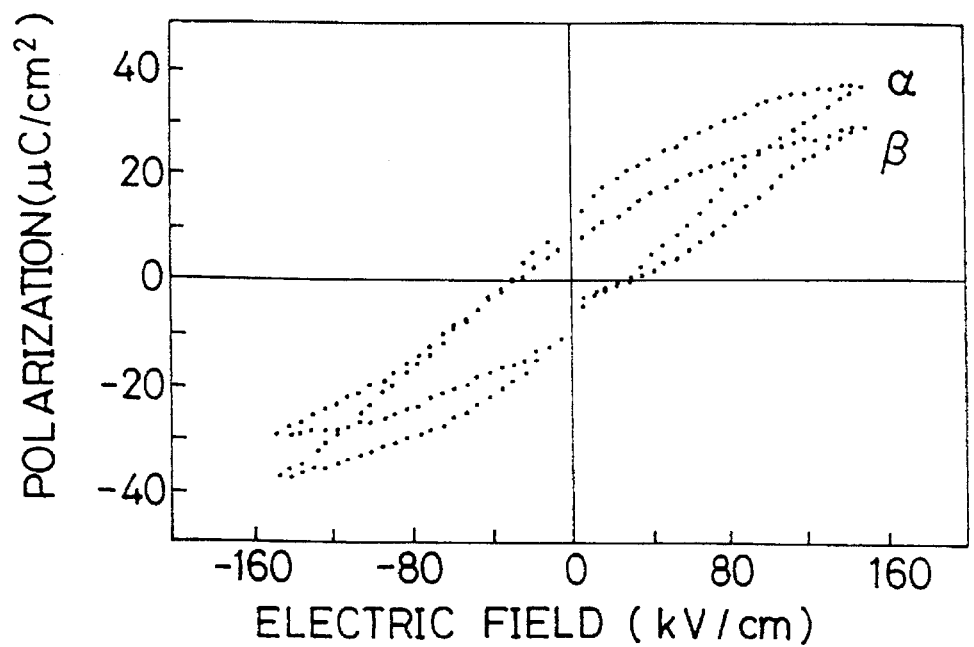
Figure 7:
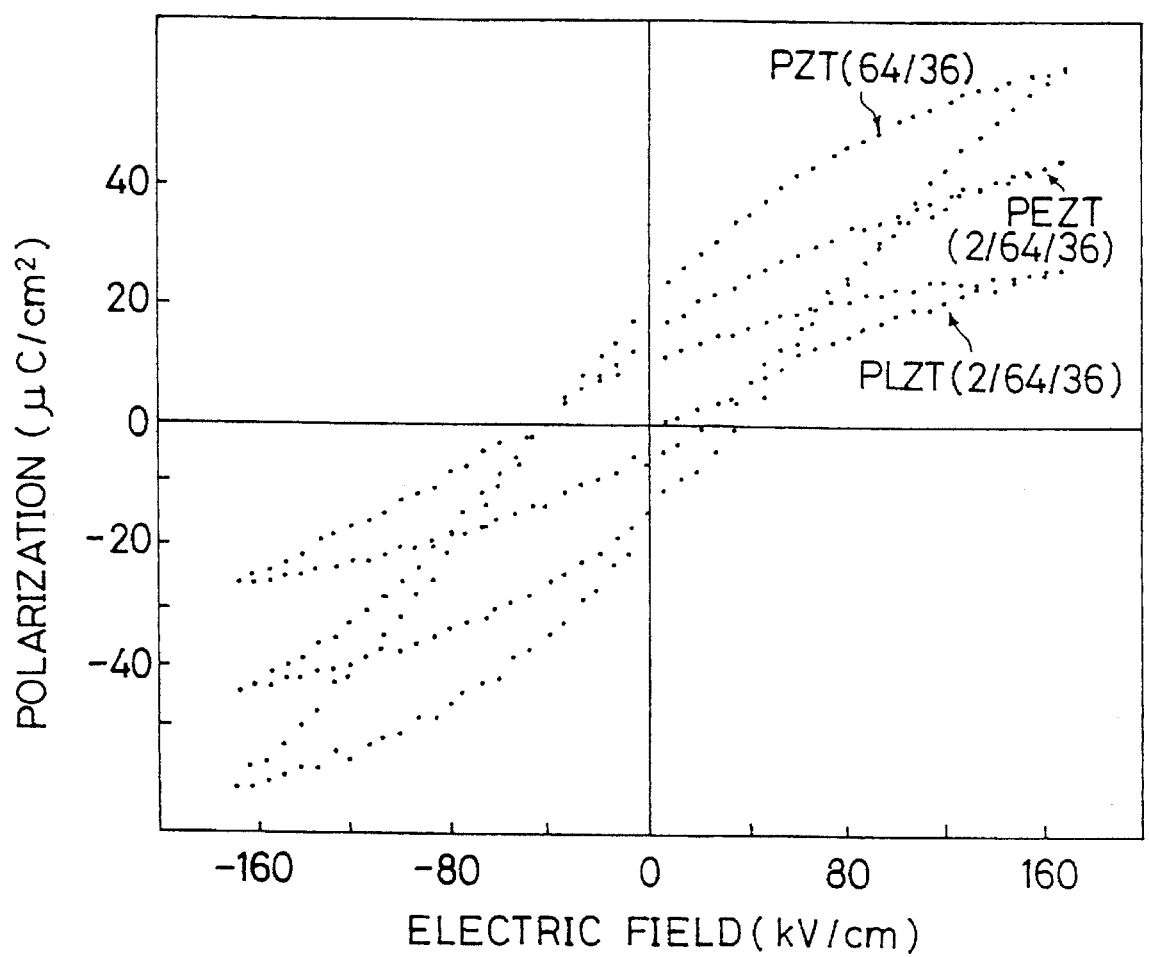
FIG. 7 is a graph showing the change in hysteresis loop caused by adding lanthanum (La) and erbium (Er) to PZT.

In contrast to this, FIG. 6b shows the measured results of the fatigue characteristics of a general dielectric thin film element manufactured for comparison and constructed by PZT when y=0. As shown in FIG. 6b, this dielectric thin film element shows ferroelectricity drawing a hysteresis loop γ in which the remanent polarization is initially 16.97 (μC/cm$^2$) and the coercive field is 38.41 (kV/cm). After the polarization of the dielectric thin film element is inverted 108 times as mentioned above, the dielectric thin film element provides a hysteresis loop δ in which the remanent polarization is 6.39 (μC/cm$^2$). Accordingly, the remanent polarization is greatly reduced by 10 (μC/cm$^2$) or more. This reduction thus indicates greater fatigue. From these results, it can be understood that the dielectric thin film element in this embodiment has excellent fatigue characteristics in comparison with a general dielectric thin film element. The measured results of the fatigue characteristics of the dielectric thin film element manufactured in this embodiment are shown when y is equal to 0.01. However, the dielectric thin film element in this embodiment similarly has excellent electrical fatigue characteristics when y is equal to 0.02 and 0.05. The case of y=0.02 is shown in FIG. 6c and the case of y=0.05 is shown in FIG. 6d. Lanthanum (La) is already known as an element added to PZT. Similar to erbium (Er), lanthanum (La) can be used to reduce the leakage current. However, as shown in FIG. 7, lanthanum (La) has a problem that initial characteristics of the remanent polarization are greatly reduced in comparison with erbium (Er).

In a dielectric thin film element similar to that in the above embodiment, effects similar to those in the above embodiment can be obtained even when the erbium composition ratio is reduced to about 0.1 (y=0.001) by changing only this erbium composition ratio. When the erbium composition ratio is increased beyond 5 (y=0.05), the ferroelectricity decreases, but the dielectric thin film element shows a high dielectric constant as a paraelectric material. For example, when the dielectric thin film element is measured by an LCR meter with a frequency of 1 kHz and an applied voltage of ±100 mV, the obtained dielectric constant of the dielectric thin film element is equal to 1036. Accordingly, the dielectric thin film element having excess erbium cannot be used as a thin film element using ferroelectricity, but can be used as a dielectric thin film element having a high dielectric constant.

In the above embodiment, the sol-gel method is used as a method for manufacturing the PEZT dielectric thin film. However, the present invention is not limited to this sol-gel method. For example, a vacuum evaporation method, a sputtering method, a metal organic chemical vapor deposition growing method (MOCVD method), etc. may be also used as a method for manufacturing the PEZT dielectric thin film. In the above embodiment, a constant ratio of Zr:Ti= 64:36 is set in the composition ratio of the PEZT dielectric thin film. However, the present invention is not limited to this constant ratio.

In the above first embodiment, the dielectric thin film element is constructed by a dielectric thin film based on the present invention and is manufactured to evaluate the electrical characteristics of the dielectric thin film element. The present invention is also used with respect to a substrate other than the PEZT dielectric thin film, film materials, film thicknesses, etc. The present invention is further used in a concrete electronic element structure in each of the following embodiments, but is not limited to this element structure and the element structure in the above first embodiment.

In the following embodiments, the PEZT dielectric thin film is used in various kinds of electronic elements. These embodiments will be explained.

Figure 8A:
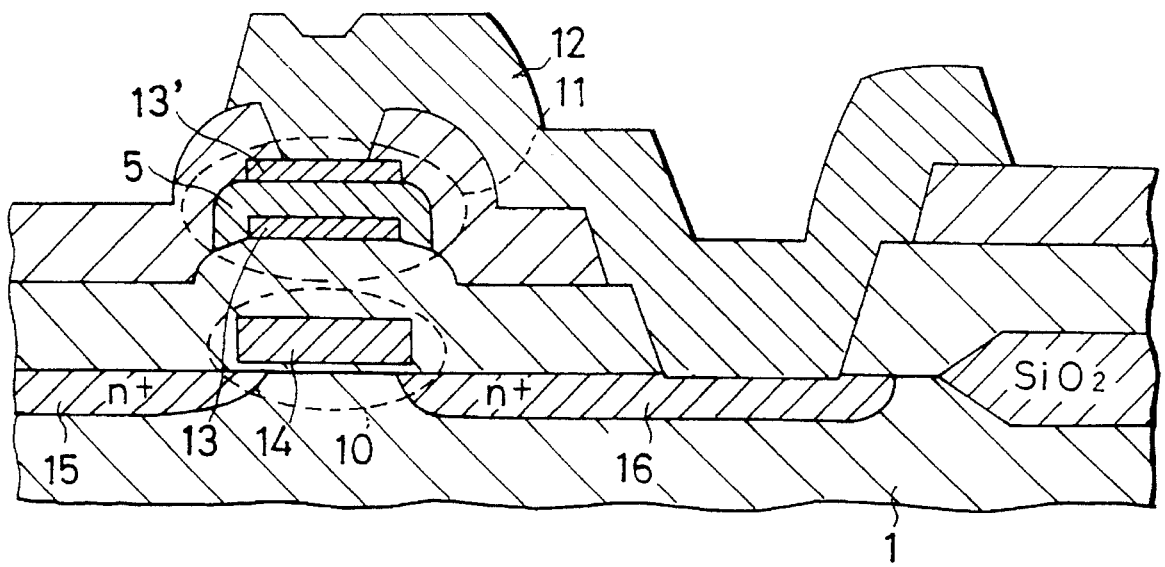
FIG. 8a is a cross-sectional view schematically showing the structure of a non-volatile memory having a capacitor structure using the dielectric thin film element in the above embodiment.
Figure 8B:
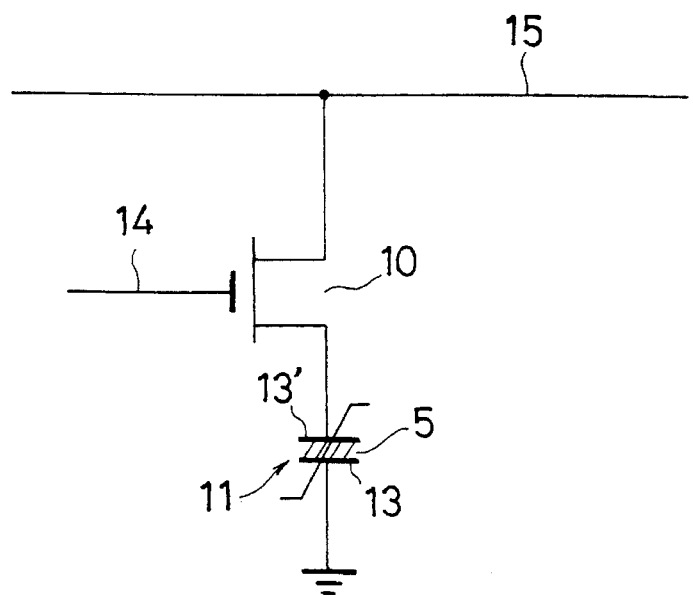
FIG. 8b is a diagram showing an electric circuit equivalent to the non-volatile memory having the capacitor structure using the dielectric thin film element in the above embodiment.

In the second embodiment of the present invention, the dielectric thin film in the above first embodiment is used as a non-volatile memory having a capacitor structure. This second embodiment will first be explained with reference to FIG. 8a and FIG. 8b showing an electric circuit equivalent to the non-volatile memory.

In the non-volatile memory having the capacitor structure using the above dielectric thin film 5, one memory cell is constructed using one capacitor 11 and one transistor 10. The capacitor 11 is composed of a PEZT ferroelectric thin film 5 and a pair of conductors (electrodes) 13, 13' for supporting the PEZT ferroelectric thin film 5 therebetween. The transistor 10 is composed of a bit line 15, a word line 14 and a signal line 16 connected to an aluminum (Al) electrode 12. The aluminum (Al) electrode 12 is also connected to the capacitor electrode 13'.

A method for manufacturing the non-volatile memory having the above capacitor structure will be described. First, a $SiO_2$ layer and a $Si_3N_4$ layer are formed on a n-type silicon substrate 1. The region where transistors are to be formed is defined by photolithography and surrounding $Si_3N_4$ layer is removed. Then, the exposed $SiO_2$ layer is grown by field oxidation. The $Si_3N_4$ and $SiO_2$ film below it are then removed. A gate $SiO_2$ layer is formed by a gate oxidization. After that, a Poly-Silicon gate 14 is formed. Ions are implanted into the silicon substrate using this Poly-Silicon gate 14 as a mask so that a source 15 and a drain are formed. A surface of the silicon substrate is covered with a phospho silicate glass (PSG) and flattened by a re-flow. An electrode 13 is formed on this PSG. A PEZT ferroelectric thin film 5 is then formed on the electrode 13. An electrode 13' is further formed on this PEZT ferroelectric thin film 5 and is covered with a PSG layer. After reflow, contact holes are formed on the electrode 13' and the drain 16 by etching. An aluminum (Al) electrode 12 for connecting is finally deposited on the etched portion.

The operation of the non-volatile memory having the above capacitor structure will next be explained.

When value "1" is written to the non-volatile memory, a negative pulse equal to or stronger than the strength of a coercive field is applied to the ferroelectric thin film 5 through the transistor 10 on the bit line 15. In this case, dielectric polarization is induced in the ferroelectric thin film 5 and negative polarizing charges are accumulatively stored on the electrode 13 of the capacitor 11. In contrast to this, when value "0" is written to the non-volatile memory, a positive pulse equal to or stronger than the strength of the coercive field is applied to the ferroelectric thin film 5 through the transistor 10 on the bit line 15. In this case, positive polarizing charges are accumulatively stored on the electrode 13 of the capacitor 11.

When the value "1" is read from the non-volatile memory, a positive pulse is applied to the ferroelectric thin film 5. In this case, polarization of the negative charges is inverted so that positive polarizing charges are accumulatively stored on the electrode 13 of the capacitor 11. Accordingly, a difference in charge amount is seen between the positive and negative residual polarizing charges before and after the application of the pulse. In contrast to this, when the value "0" is read from the non-volatile memory, no polarization inversion is detected even when the positive pulse is applied to the ferroelectric thin film 5. Accordingly, there is almost no change in charge amount before and after the application of the pulse. Therefore, bit information is determined by detecting this difference in charge amount by using a sense amplifier connected to the bit line.

Since the ferroelectric thin film 5 has residual polarizing charges, the value "1" or "0" is held even when a power source of the non-volatile memory is turned off. Accordingly, a non-volatile memory operation is realized.

In a structure similar to the above capacitor structure, the DRAM can be operated by using only a ferroelectric material with a high dielectric constant, and can be operated as a non-volatile memory only when a power source of the DRAM is turned off.

In this second embodiment, a molar fraction of erbium is preferably set to 0.5 to 5.0 mol %. Since the abovementioned PEZT thin film shows an orientating direction of the crystal in which (111) is main peak and the polarizing axis of a rhombic faced crystal is (111), a Zr/Ti ratio is preferably ranged from 52/48 to 70/30 so that an orientating direction of the crystal is in conformity with a polarizing direction and remanent polarization is set to $Pr \geq 10$ μC/cm$^2$.

In a third embodiment of the present invention, the dielectric thin film in the first embodiment is used in a MFMIS-FET (metal ferroelectric metal insulator semiconductor-FET). This third embodiment will be explained with reference to FIG. 9.

Figure 9:
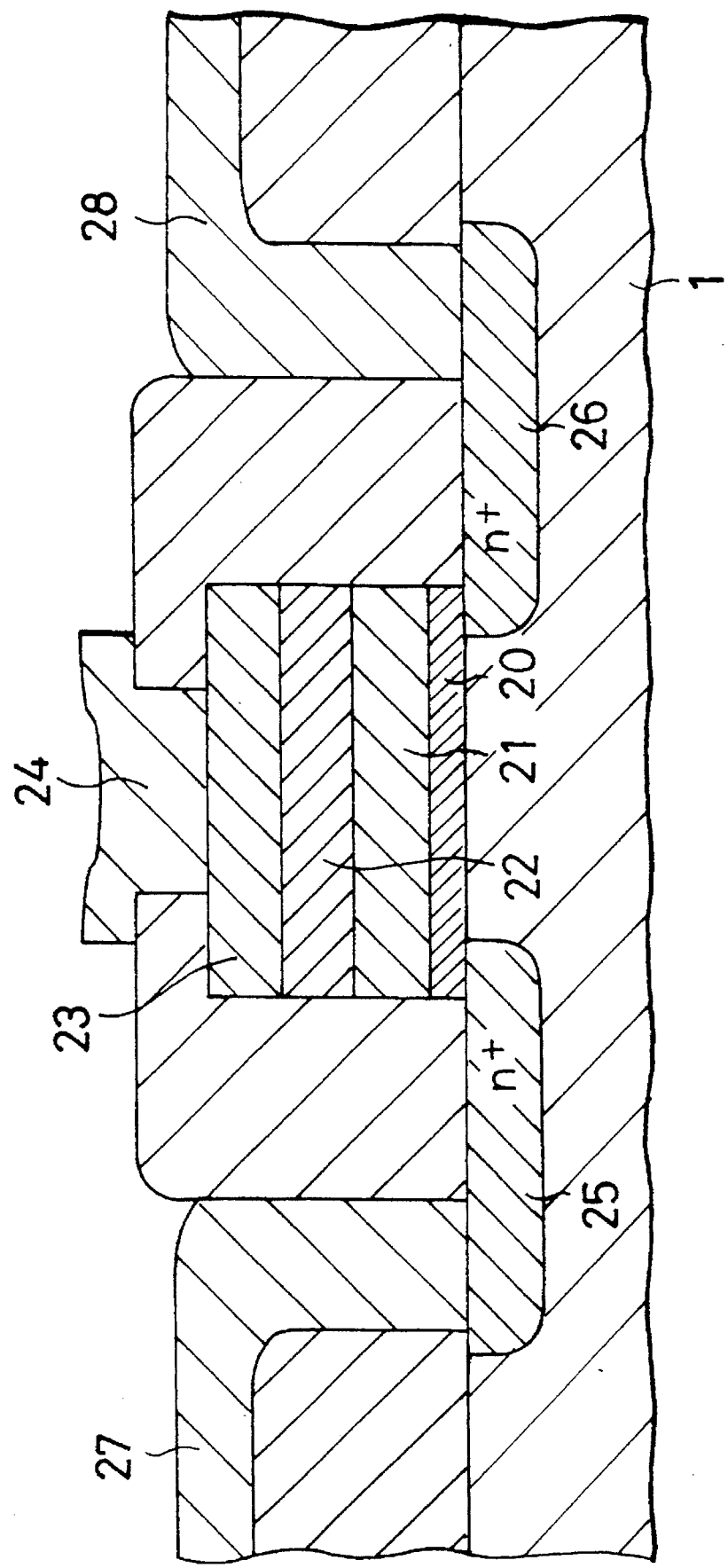
FIG. 9 is a cross-sectional view schematically showing the structure of a MFMIS-FET using the dielectric thin film element in the above embodiment.

FIG. 9 is a cross-sectional view showing a schematic construction of the MFMIS-FET using the dielectric thin film in the third embodiment. A gate SiO$_2$ layer 20 is formed by the same method described for fabricating the device shown in FIG. 8a. A floating gate layer 21 made of platinum (Pt) is then formed. A drain 25 and source 26 are formed by an ion implantation. The surface of silicon substrate is covered with PSG and flattened by re-flow.

Next, the PSG layer on platinum (Pt) gate layer 21 is removed by etching. A PEZT ferroelectric thin film 22 is formed. A control gate 23 made of platinum (Pt) is formed on this PEZT ferroelectric thin film 22.

Thereafter, a surface of the silicon substrate is then covered with a PSG layer and flattened by a re-flow. Contact holes are formed on the control gate 23, the drain 25, and the source 26 by etching. Aluminum electrodes 24, 27, and 28 for connecting are finally deposited thereon.

In the MFMIS-FET, a voltage is applied to the control gate 23 and the polarizing direction of the above ferroelectric thin film is changed. The SiO$_2$ film 20 as a gate insulating film is also dielectrically polarized by this electrostatic induction through the floating gate 21 so that a polarizing direction of the SiO$_2$ film 20 is changed. Formation of a channel on the semiconductor surface just below the gate can be controlled by this polarizing direction. Accordingly, signal values "0" and "1" can be defined by performing turning-on and turning-off operations of the drain current.

For example, in a zero bias state of the gate electrode 24, the ferroelectric thin film 22 is polarized in an extending direction of the semiconductor substrate such that the floating gate 21 has a negative polarity. In this case, the SiO$_2$ film 20 is dielectrically polarized and the face in contact with the silicon substrate 1 has a negative polarity. The surface of the silicon substrate 1 in contact with the SiO$_2$ film 20 has a positive polarity. The drain 25 and the source 26 are then not connected to each other, thereby attaining a turning-off state.

Next, a positive voltage greater than the coercive field of the ferroelectric thin film 22 is applied to the gate electrode 24. Thus, the polarizing direction of the ferroelectric thin film 22 is inverted such that the floating gate 21 has a positive polarity. In this case, the SiO$_2$ film 20 is dielectrically polarized and the face in contact with the silicon substrate 1 has a positive polarity. The face of the silicon substrate 1 in contact with the SiO$_2$ film 20 has a negative polarity so that the drain 25 and the source 26 are connected to each other, thereby attaining a turning-on state.

This turning-on state is held by residual polarization even when the gate voltage is set to a zero bias state.

The dielectric polarization of this SiO$_2$ film 20 is held as long as polarization of the dielectric thin film 22 is held. Accordingly, the above memory can be operated as a nonvolatile memory capable of performing a nondestructive reading operation.

In this third embodiment, the molar fraction of erbium (Er) is preferably set to 0.5 to 5.0 mol %. The Zr/Ti ratio is preferably ranged from 45/55 to 80/20 to provide remanent polarization Pr equal to several μC/cm$^2$.

Figure 10A:
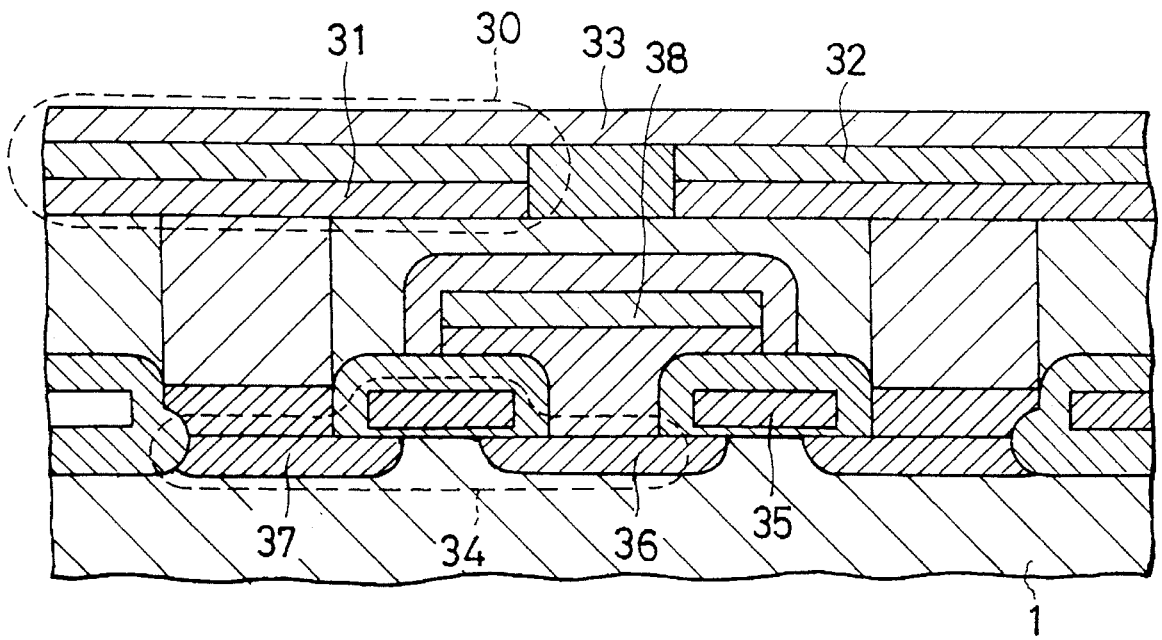
FIG. 10a is a cross-sectional view schematically showing the structure of a flattened STC-type DRAM using the dielectric thin film element in the above embodiment.
Figure 10B:
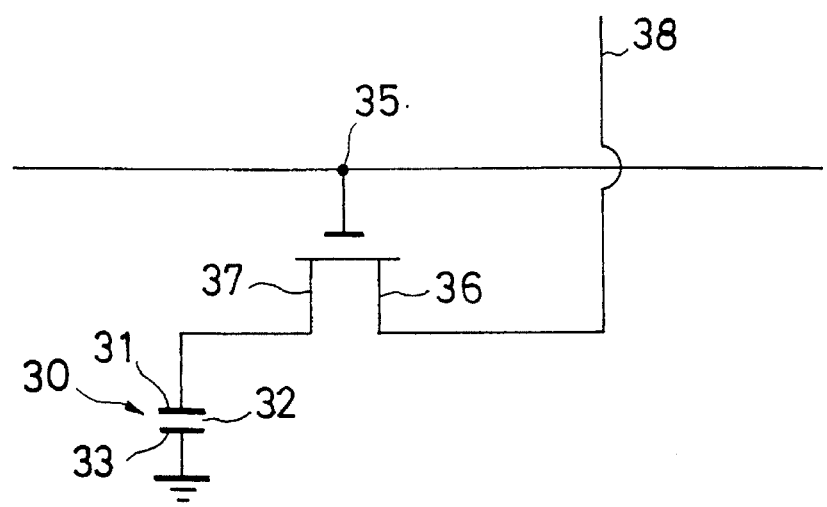
FIG. 10b is a diagram showing an electric circuit equivalent to the flattened STC-type DRAM using the dielectric thin film element in the above embodiment.

In a fourth embodiment of the present invention, a dielectric thin film is used in a flattened STC-type DRAM. This fourth embodiment will next be explained with reference to FIG. 10a and FIG. 10b showing an electric circuit equivalent to this DRAM.

In the flattened STC-type DRAM, a dielectric thin film 32 showing high dielectric constant characteristics in the first embodiment is formed as a capacitor insulating film on a lower electrode 31 formed on a silicon substrate 1. A plate electrode 33 is subsequently formed on this dielectric thin film 32 so that a capacitor 30 is formed.

A transistor 34 is formed with a word line 35, a source 36 and a drain 37. The source 36 is connected to a bit line 38.

The operation of the flattened STC-type DRAM having the above construction will next be explained.

When data are written to this DRAM, data inputted from the bit line 38 are written to the capacitor 30 through the transistor 34. In contrast to this, when these data are read from the DRAM, a voltage is applied to the word line 35 corresponding to a read memory cell so that data are outputted from the capacitor 30 to the bit line 38 through the transistor 34.

Since the dielectric thin film 32 showing high dielectric constant characteristics is used, the area for the capacitor cell is reduced by 1/500 or more at the same thickness in comparison with a case in which a silicon dioxide film is used as the capacitor insulating film. Accordingly, the DRAM can be highly integrated.

In this fourth embodiment, a molar faction of erbium (Er) is preferably set to 5.0 to 10.0 mol % providing a range of reduced remanent polarization. Further, a Zr/Ti ratio is also preferably ranged from 45/55 to 75/25 to provide this range.

Figure 11:
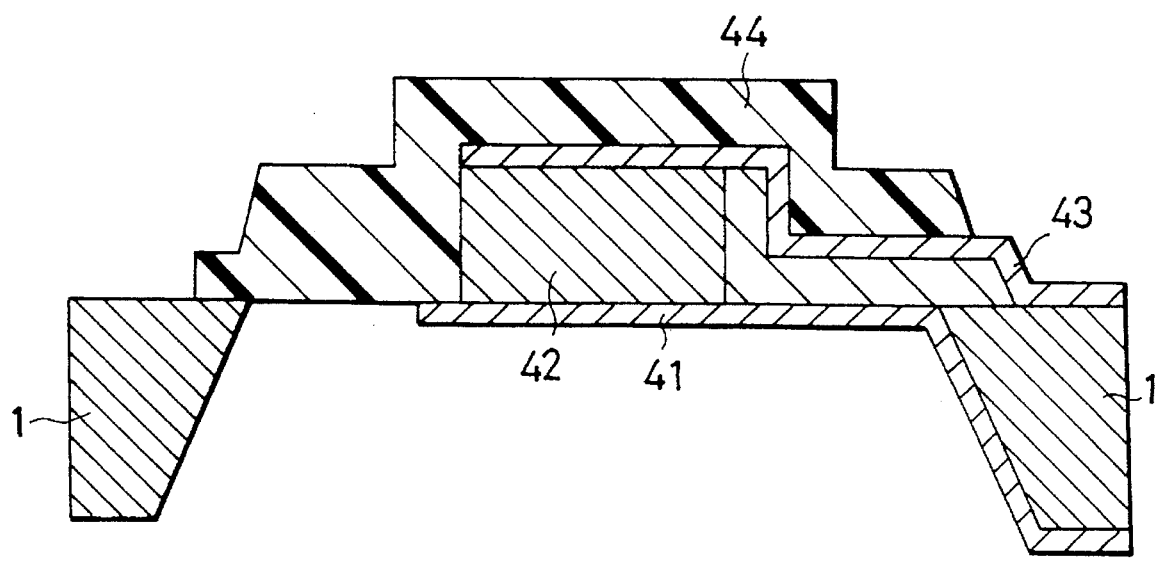
FIG. 11 is a cross-sectional view schematically showing the structure of an pyroelectric infrared linear array sensor using the dielectric thin film element in the above embodiment.

In a fifth embodiment of the present invention, a dielectric thin film is used in a pyroelectric infrared linear array sensor. This fifth embodiment will be explained with reference to FIG. 11.

This infrared linear array sensor has a dielectric thin film 42, a Ni-Cr light receiving electrode 41, an array electrode 43 and a resin protecting film 44. The dielectric thin film 42 is supported by the Ni-Cr light receiving electrode 41 and the array electrode 43 therebetween.

A method for manufacturing the above infrared linear array sensor will next be described.

A dielectric thin film 42 is formed on a silicon substrate 1 and is then etched to form the detector pixel. A silicon dioxide layer is then formed on the etched portion of the dielectric thin film 42. The pattern of an array electrode 43 is next formed on this silicon dioxide layer by mask etching. The dielectric thin film 42 is exposed by etching the silicon substrate 1 from below. A Ni-Cr light receiving electrode 41 is formed on an exposed portion of the dielectric thin film 42. The dielectric thin film 42 and the array electrode 43 are covered with a resin protecting film 44.

The infrared linear array sensor uses the pyroelectric effect of the dielectric thin film 42 in which charges are generated on the surface of the dielectric thin film 42 as a result of a change in temperature of this film. When an infrared ray is incident onto the surface of the dielectric thin film 42, the temperature of the dielectric thin film 42 is changed so that a voltage or a pyroelectric current is caused. The infrared ray is detected by detecting this voltage or pyroelectric current.

In this fifth embodiment, the molar faction of erbium (Er) is preferably set to 0.5 to 10.0 mol % showing a pyroelectric range. Further, a Zr/Ti ratio is preferably ranged from 45/55 to 75/25 to provide this range.

Figure 12A:
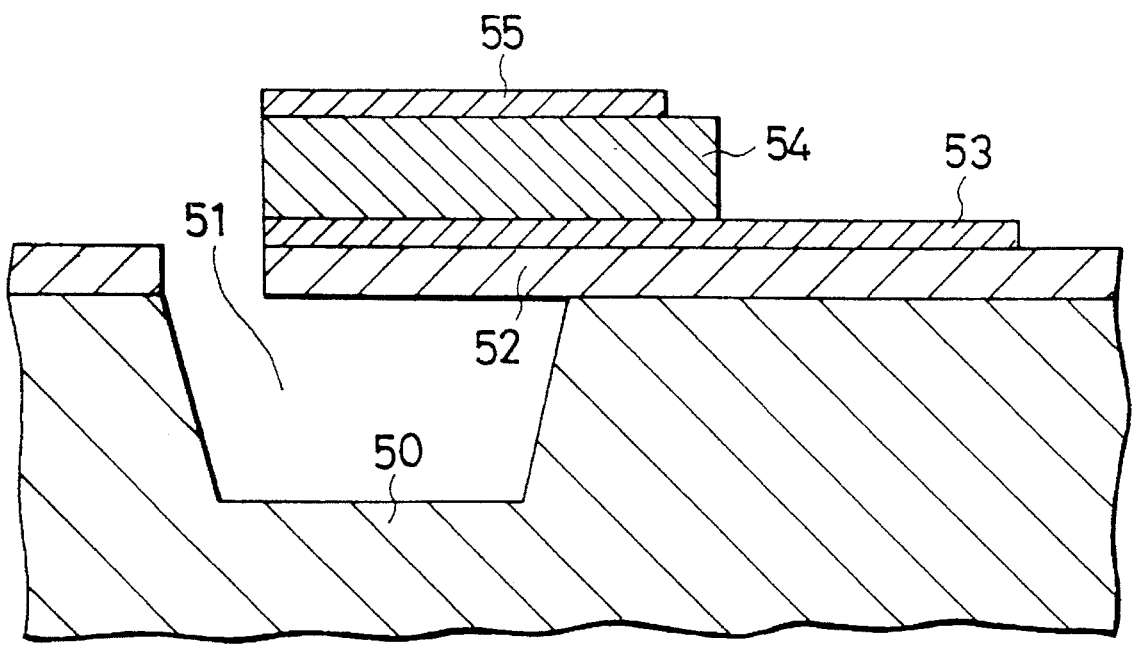
FIG. 12a is a cross-sectional view schematically showing the structure of a piezoelectric sensor using the dielectric thin film element in the above embodiment.
Figure 12B:
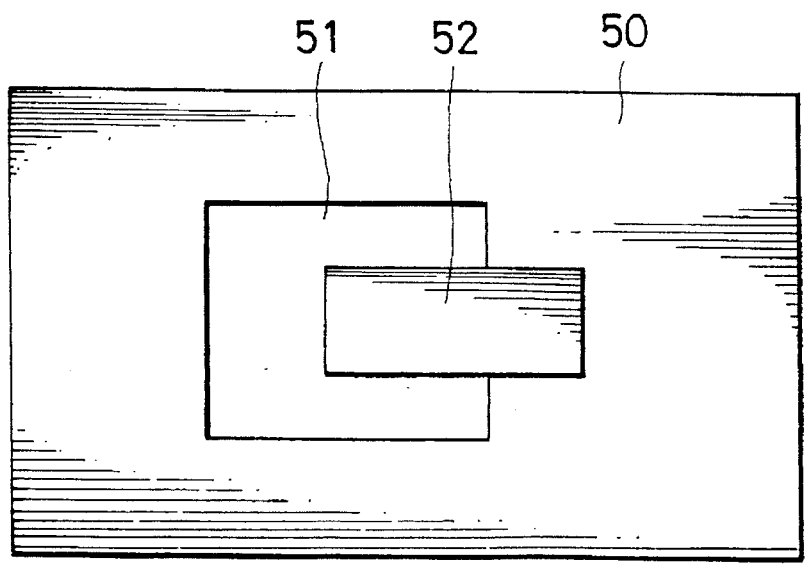
FIG. 12b is a plan view of the piezoelectric sensor using the dielectric thin film element in the above embodiment.

In a sixth embodiment of the present invention, a dielectric thin film is used in a piezoelectric sensor, This sixth embodiment will be explained with reference to FIG. 12a and FIG. 12b.

A piezoelectric sensor has a silicon substrate 50 having a recessed portion 51. The cantilever beam 52 is formed by a silicon dioxide film on the silicon substrate 50. The end tip of the cantilever beam 52 is located in an upper portion of the recessed area 51. A platinum (Pt)/titanium (Ti) electrode 53 is laminated and formed on the cantilever beam 52. A dielectric thin film 54 is laminated and formed on the Pt/Ti electrode 53. An aluminum (Al) electrode 55 is laminated and formed on the dielectric thin film 54. At the time of fabrication of the piezoelectric sensor, the cantilever beam 52 is first formed and the recessed portion 51 is then formed by etching.

The piezoelectric sensor measures an ultrasonic wave by the piezoelectric effect of the dielectric material as a phenomenon in which the electrical polarization is proportional to the mechanical stress. When the ultrasonic wave is incident on the piezoelectric sensor, the cantilever beam 52 resonates by sound pressure of this ultrasonic wave so that the dielectric thin film 54 is flexed. A voltage is caused between the electrodes 53 and 55 by piezoelectric effect provided by flexing the dielectric thin film 54. The resonance frequency can be easily controlled by changing the size of the cantilever beam 52 or the film thickness.

In this sixth embodiment, a molar faction of erbium (Er) is preferably set to 0.5 to 10.0 mol % showing a piezoelectric range. Further, a Zr/Ti ratio is preferably ranged from 45/55 to 75/25 to provide this range.

Figure 13A:
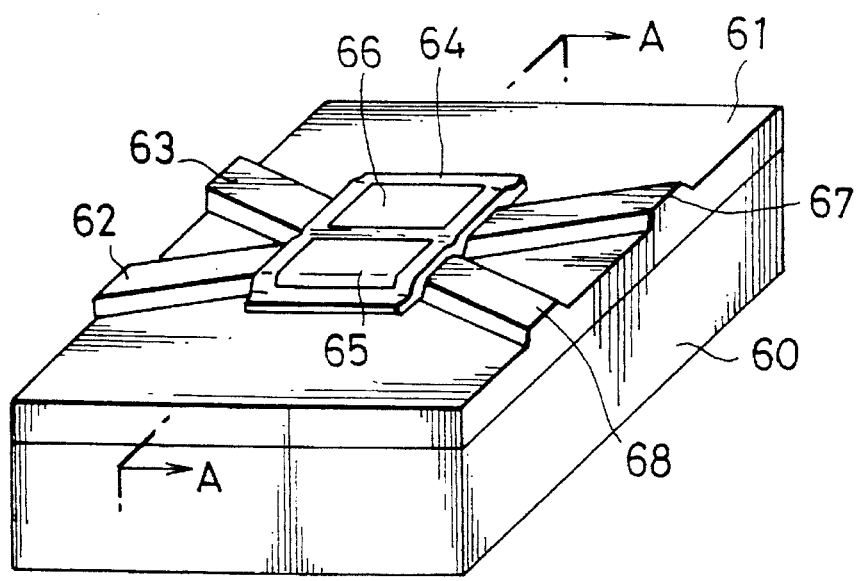
FIG. 13a is a perspective view of an optical waveguide modulator using the dielectric thin film element in the above embodiment.
Figure 13B:
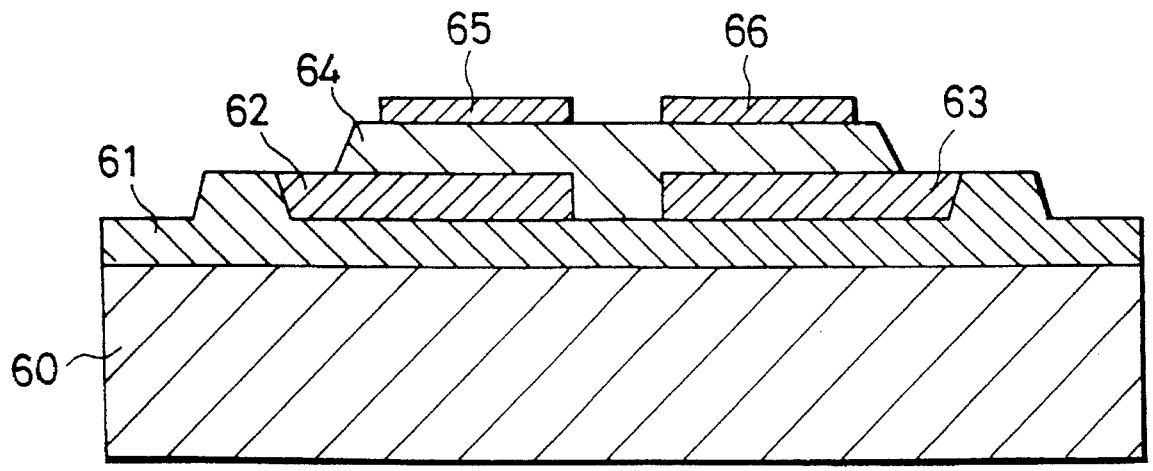
FIG. 13b is a cross-sectional view showing a schematic structure of the optical waveguide modulator using the dielectric thin film element in the above embodiment.

In a seventh embodiment of the present invention, a dielectric thin film is used in an optical modulator of a waveguide type. This seventh embodiment will be explained with reference to FIG. 13a and FIG. 13b.

The optical modulator of the waveguide type uses the electrooptic effect of a dielectric material as a phenomenon in which a refractive index of the dielectric material is changed by applying an electric field to the dielectric material.

The optical modulator of the waveguide type has a sapphire substrate 60. A PEZT dielectric thin film 61 is laminated and formed on the sapphire substrate 60. Ports 62, 63, 67 and 68 are laminated and formed on the dielectric thin film 61. A buffer layer 64 is laminated and formed on the ports 62, 63, 67 and 68 such that the ports 62 and 63 are separated from each other and the ports 67 and 68 are separated from each other. Aluminum (Al) electrodes 65 and 66 are respectively laminated and formed on the buffer layer 64 in a position opposed to the ports 62 and 68 and a position opposed to the ports 63 and 67. In the optical modulator, two waveguides cross each other and the electrodes 65 and 68 having small gaps are arranged in the central crossing portion of the waveguides. The port 67 is arranged in an extending direction of the port 62 through the buffer layer thereof. The port 68 is arranged in an extending direction of the port 63 through the buffer layer thereof. When a voltage is applied to the electrodes 65 and 66, the refractive index of the optical modulator is locally changed by an electric field concentrated in the gaps so that light is totally reflected on this local portion.

As one example, let us consider a case in which light is inputted to the optical modulator through the port 62. When no voltage is applied to the electrode 66, light is transmitted directly to port 68. In contrast to this, when a voltage is applied to the electrode 66, light is totally reflected on the optical modulator and is outputted from the port 67.

In this seventh embodiment, a molar faction of erbium (Er) is preferably set to 0.5 to 10.0 mol % showing an electrooptic range. Further, a Zr/Ti ratio is preferably ranged from 45/55 to 75/25 to provide this range.

As mentioned above, erbium lead zirconate titanate represented by $(Pb_{1-y}Er_y)(Zr_xTi_{1-x})O_3$ is used for a dielectric thin film in the present invention. Accordingly, the leakage current can be reduced and electric fatigue characteristics can be improved. When this dielectric thin film is used, it is possible to provide a memory element having high performance such as a non-volatile memory element showing ferroelectricity and a DRAM having high dielectric constant characteristics, etc. Further, it is possible to provide an infrared sensor, a piezoelectric sensor and a waveguide switch of a total reflecting type having excellent characteristics.

Many widely different embodiments of the present invention may be constructed without departing from the spirit and scope of the present invention. It should be understood that the present invention is not limited to the specific embodiments described in the specification, except as defined in the appended claims.

What is claimed is:

1. A dielectric thin film element comprising a dielectric thin film comprising lead erbium zirconate titanate represented by $(Pb_{1-y}Er_y)(Zr_xTi_{1-x})O_3$ and $0<x<1$ and $0<y<1$.

2. A dielectric thin film element as claimed in claim 1, wherein $0.45 \leq x \leq 0.8$ and $0.005 \leq y \leq 0.05$ are set with respect to said lead erbium zirconate titanate represented by $(Pb_{1-y}Er_y)(Zr_xTi_{1-x})O_3$, and said dielectric thin film shows ferroelectricity.

3. A dielectric thin film element as claimed in claim 1, wherein $0.45 \leq x \leq 0.75$ and $0.05 \leq y \leq 0.1$ are set with respect to said lead erbium zirconate titanate represented by $(Pb_{1-y}Er_y)(Zr_xTi_{1-x})O_3$, and said dielectric thin film has a dielectric constant higher than that of silicon oxide or silicon nitride.

4. A dielectric thin film element comprising a thermally grown silicon dioxide film, a titanium film, a platinum lower electrode, a film of erbium lead zirconate titanate represented by $(Pb_{1-y}Er_y)(Zr_xTi_{1-x})O_3$ and a platinum upper electrode which are sequentially formed on an n-type silicon substrate;

$0.45 \leq x \leq 0.8$ and $0.005 \leq y \leq 0.1$ being set.

5. A non-volatile memory combined with a switching transistor using a dielectric thin film as a capacitor insulating layer connected to a MOS transistor;

the dielectric thin film being constructed from lead erbium zirconate titanate represented by $(Pb_{1-y}Er_y)(Zr_xTi_{1-x})O_3$; and $0.52 \leq x \leq 0.7$ and $0.005 \leq y \leq 0.05$ being set.

6. A metal ferroelectric metal insulator semiconductor FET as a MFMIS-FET in which a dielectric thin film is buried as an insulating gate film of a field effect transistor;

the dielectric thin film being constructed from lead erbium zirconate titanate represented by $(Pb_{1-y}Er_y)(Zr_xTi_{1-x})O_3$; and $0.45 \leq x \leq 0.8$ and $0.005 \leq y \leq 0.05$ being set.

7. A flattened STC-type DRAM comprising a number of memory cells each constructed by one transistor and a capacitor;

said capacitor having a dielectric thin film of lead erbium zirconate titanate represented by $(Pb_{1-y}Er_y)(Zr_xTi_{1-x})O_3$; and $0.45 \leq x \leq 0.75$ and $0.05 \leq y \leq 0.1$ being set.

8. An infrared linear array sensor of a pyroelectric thin film type comprising a light receiving electrode, a dielectric thin film and an array electrode sequentially formed to detect an infrared ray;

the dielectric thin film being constructed from lead erbium zirconate titanate represented by $(Pb_{1-y}Er_y)(Zr_xTi_{1-x})O_3$; and $0.45 \leq x \leq 0.75$ and $0.005 \leq y \leq 0.1$ being set.

9. A piezoelectric sensor comprising a cantilever beam, a first electrode, a dielectric thin film and a second electrode sequentially formed;

the dielectric thin film being constructed from lead erbium zirconate titanate represented by $(Pb_{1-y}Er_y)(Zr_xTi_{1-x})O_3$; and $0.45 \leq x \leq 0.75$ and $0.005 \leq y \leq 0.1$ being set.

10. An optical modulator of a waveguide type comprising a dielectric thin film, a buffer layer and two separated metallic electrodes formed on a substrate at the crossing point of two waveguides;

the dielectric thin film being constructed from lead erbium zirconate titanate represented by $(Pb_{1-y}Er_y)(Zr_xTi_{1-x})O_3$; and $0.005 \leq x \leq 0.1$ and $0.45 \leq y \leq 0.75$ being set.

* * * * *